(12) United States Patent
Kasai et al.

(10) Patent No.: US 7,422,672 B2
(45) Date of Patent: Sep. 9, 2008

(54) CAPILLARY ARRAY APPARATUS, METHOD OF MANUFACTURING THE SAME, AND ELECTROPHORESIS ANALYSIS METHOD

(75) Inventors: Syozo Kasai, Hitachinaka (JP); Takayasu Furukawa, Hitachinaka (JP); Ryoji Inaba, Hitachinaka (JP); Daiki Numai, Hitachinaka (JP); Tomoyuki Tobita, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 631 days.

(21) Appl. No.: 10/732,221

(22) Filed: Dec. 11, 2003

(65) Prior Publication Data
US 2004/0144652 A1 Jul. 29, 2004

(30) Foreign Application Priority Data
Dec. 12, 2002 (JP) ............................. 2002-361107

(51) Int. Cl.
*G01N 27/453* (2006.01)
(52) U.S. Cl. .................. 204/604; 204/453; 204/603
(58) Field of Classification Search ................ 204/450, 204/600, 451, 455, 601, 605, 452, 603
See application file for complete search history.

(56) References Cited

U.S. PATENT DOCUMENTS

| | | | | |
|---|---|---|---|---|
| 3,639,789 A | * | 2/1972 | Bednarski | 310/43 |
| 4,885,076 A | * | 12/1989 | Smith et al. | 204/451 |
| 4,898,658 A | * | 2/1990 | Karger et al. | 204/603 |
| 5,221,448 A | * | 6/1993 | Weinberger et al. | 204/452 |
| 5,239,360 A | * | 8/1993 | Moring et al. | 356/344 |
| 5,244,560 A | * | 9/1993 | Kuhr | 204/601 |
| 5,458,761 A | * | 10/1995 | Kamahori et al. | 204/602 |
| 5,784,154 A | * | 7/1998 | Pawliszyn | 356/128 |
| 5,885,430 A | * | 3/1999 | Kernan et al. | 204/453 |
| 5,958,202 A | * | 9/1999 | Regnier et al. | 204/451 |
| 6,572,752 B1 | * | 6/2003 | Maeshima et al. | 204/601 |
| 6,878,256 B2 | * | 4/2005 | Kasai et al. | 204/604 |
| 2001/0040095 A1 | * | 11/2001 | Shimizu et al. | 204/603 |
| 2002/0023839 A1 | * | 2/2002 | Inaba et al. | 204/451 |
| 2003/0127328 A1 | * | 7/2003 | Nordman et al. | 204/451 |

(Continued)

FOREIGN PATENT DOCUMENTS

JP 10-019846 1/1998

(Continued)

OTHER PUBLICATIONS

Machine generated translation of JP 10-206382, Aug. 1998.*

*Primary Examiner*—Kaj K Olsen
(74) *Attorney, Agent, or Firm*—Dickstein Shapiro LLP

(57) ABSTRACT

An electrophoresis analysis method and apparatus capable of maintaining high reliability upon a repeated use of the same gel. A heat transfer medium selected from the group consisting of solids, liquids and gels is filled in substantially all of the gaps between the electrode and each capillary. A hollow electrode into which a capillary is inserted has a plurality of retaining shapes such that the capillary can be fixed at the center of the electrode. The heat from the capillary can be efficiently dissipated via the electrode, and also the temperature increase in the capillary can be prevented. Further, temperature increases due to the heating of the capillaries during operation can be controlled and thereby thermal deterioration of the gel can be prevented.

4 Claims, 9 Drawing Sheets

U.S. PATENT DOCUMENTS

2003/0226756 A1 * 12/2003 Inaba et al. .................. 204/601
2004/0173460 A1 * 9/2004 Yamamoto et al. .......... 204/601

FOREIGN PATENT DOCUMENTS

| JP | 10-206382 | * | 8/1998 |
| JP | 2001-004593 A | | 1/2001 |
| JP | 2001-165904 A | | 6/2001 |
| WO | WO 02/090968 A1 | | 11/2002 |

* cited by examiner (a)   (b)

CAPILLARY ARRAY APPARATUS, METHOD OF MANUFACTURING THE SAME, AND ELECTROPHORESIS ANALYSIS METHOD

FIELD OF THE INVENTION

The present invention relates to a capillary array apparatus for separating and analyzing a sample such as DNA or protein, and a method of manufacturing the apparatus. The invention also relates to an electrophoresis method utilizing the capillary array.

BACKGROUND OF THE INVENTION

In an existing electrophoresis apparatus and method, a plurality of capillaries are put together to form an array, and an electrophoresis medium and samples are supplied to each capillary, so that the samples can be separated by migration and then analyzed. Examples of the samples supplied to the capillaries for separation and analysis include DNA and protein labeled by a fluorescent substance.

From the viewpoint of separation or analysis throughput, there are more advantages in an electrophoresis method utilizing multiple capillaries than one utilizing a slab gel. For example, Patent Document 1 indicated below discloses a capillary array electrophoresis apparatus utilizing a capillary array made of a plurality of capillary columns that are two-dimensionally arranged and fixed by a holder. JP Patent Publication (Kokai) No. 2001-165904 discloses that each capillary is inserted into a cylindrical electrode made of stainless steel, where the gap between the cylindrical electrode and the capillary is filled by a cement, for example, such that no other samples remain therein.

SUMMARY OF THE INVENTION

However, in the multiple capillary array apparatus in which capillaries are inserted into the cylindrical electrodes as disclosed in JP Patent Publication (Kokai) No. 2001-165904, as the capillaries are made increasingly small, electrophoresis analysis sometimes results in a failure in the second and subsequent runs. The inventors have examined and analyzed this failure and the following facts have been uncovered.

While the gap between the cylindrical electrode and the capillary is filled by bonding them together by a cement, the cement never permeates into all parts of the gap between the cylindrical electrode and the capillary due to the viscosity of the cement. Specifically, while the gap at the tip portion can be filled, the remaining major portion is not, resulting instead in the formation of an air layer between the cylindrical electrode and the capillary. However, it has been sufficient if the gap at the tip portion has been filled by the cement if the purpose is only for preventing the samples from remaining in the gap.

As a result of the reduction in size of the capillaries in recent years, the amount of heat generated in the vicinity of the electrode per capillary is approximately 20 mW or more. Further, the presence of the aforementioned air layer causes the temperature of the capillary in the vicinity of the electrode to be higher than room temperature by more than several tens of degrees celsius. As a result, the gel (electrophoresis medium) comes to assume a temperature exceeding an allowable temperature and thus deteriorates, thereby adversely affecting the subsequent electrophoresis analysis.

It is therefore the object of the invention to provide an electrophoresis analysis method and apparatus capable of maintaining high reliability upon a repeated use of the same gel.

The invention provides an electrophoresis analysis apparatus in which a heat transfer medium selected from the group consisting of solids, liquids and gels is filled in substantially all parts of the gap between each electrode and capillary. The invention also provides an electrophoresis analysis apparatus and method in which a hollow electrode into which a capillary is inserted has a plurality of retaining shapes such that the capillary can be fixed at the center of the electrode. Thus, the heat from the capillary can be efficiently dissipated via the electrode, so that the temperature increase in the capillaries can be prevented.

The invention also provides an electrophoresis analysis method whereby a heat transfer medium is disposed in substantially all parts of the gap between the electrode and the capillary, such that the heat from the capillary can be dissipated via the electrode and the temperature of the capillaries can be maintained within an allowable range of the gel. Thus, the deterioration of the gel can be prevented, allowing the same gel to be used in a repeated manner for electrophoresis analysis.

More specifically, the following two features are proposed:
(1) The space between the hollow electrode pipe and the capillary is filled or molded with a synthetic resin having a better heat conductivity than air.
(2) The space between the hollow electrode pipe and the capillary is filled with a refrigerating liquid that has a better heat conductivity than air. However, one or both ends of the hollow electrode pipe are sealed to prevent the leakage of the filling liquid.

The term "hollow electrode" herein refers to an electrode shaped like a pipe. Its cross-section, however, is not limited to be circular but may be elliptical or square, for example.

The heat transfer medium used in the present invention may be selected from a variety of materials.

The synthetic resin with a better heat conductivity than air is not particularly limited. Examples include thermosetting resins, thermoplastic resins, and a variety of engineering plastics, such as epoxy resin, silicone resin, phenol resin, melamine resin, urea resin, unsaturated polyester, fluorinated resin, polyimide, polyamide-imide, polyamide such as polyetherimide, polybutylene terephthalate, polyester such as polyethylene terephthalate, polyphenylene sulfide, wholly aromatic polyester, polysulfone, liquid crystalline polymer, polyethersulfone, polycarbonate, maleimide modified resin, ABS resin, AAS (acrylonitrile-acrylic rubber-styrene) resin, AES (acrylonitrile-etylene-propylene-diene rubber-styrene) resin. Of these, an epoxy resin having two or more epoxy groups in each molecule is preferable. The epoxy resin used in the present invention is not particularly limited and may be selected from monomers, oligomers or polymers in general with two or more epoxy groups in each molecule. Examples include biphenyl-type epoxy resin, stilbene-type epoxy resin, bisphenol-type epoxy resin, triphenolmethane-type epoxy resin, alkyl-modified triphenolmethane-type epoxy resin, dicyclopentadiene-modified phenol-type epoxy resin, naphthol-type epoxy resin, and triazine nucleus-containing epoxy resin. These may be used either independently or in a mixture.

The refrigerating liquid with better heat conductivity than air may be but not particularly limited to pentafluoroethane (HFC-125), 1,1,1-trifluoroethane (HFC-143a), 1,1,1,2-tetrafluoroethane (HFC-134a), difluoromethane (HFC-32), or their mixture.

Table 1 shows the heat conductivity of various materials with reference to the heat conductivity of air 1. The comparison of heat conductivities against air in table 1 is by way of example only, and other heat transfer media may be employed in the present invention.

TABLE 1

| Name of substance | Heat conductivity | Comparative value |
|---|---|---|
| 1. air | 0.026 | 1 |
| 2. SUS304 stainless steel | 15 | 577 |
| 3. quartz | 14 | 538 |
| 4. epoxy resin | 0.214 | 8.2 |
| 5. water | 0.56 | 21.5 |
| 6. carbon-containing epoxy cement | 0.3 | 11.5 |
| 7. glycerin | 0.29 | 11 |
| 8. fluorinated inactive liquid | 0.067 | 2.6 |
| 9. alcohol | 0.22 | 8.6 |

Unit of heat conductivity: W/mK

In accordance with the invention, temperature increases by the development of heat in the capillaries during operation can be prevented, so that the thermal deterioration of gel can be prevented. As a result, DNA or proteins can be accurately and stably separated and detected.

Other novel features and effects of the invention will appear in the following description taken in connection with the accompanying drawings.

DETAILED DESCRIPTION OF THE PREFERRED EMBODIMENTS

Figure 1:
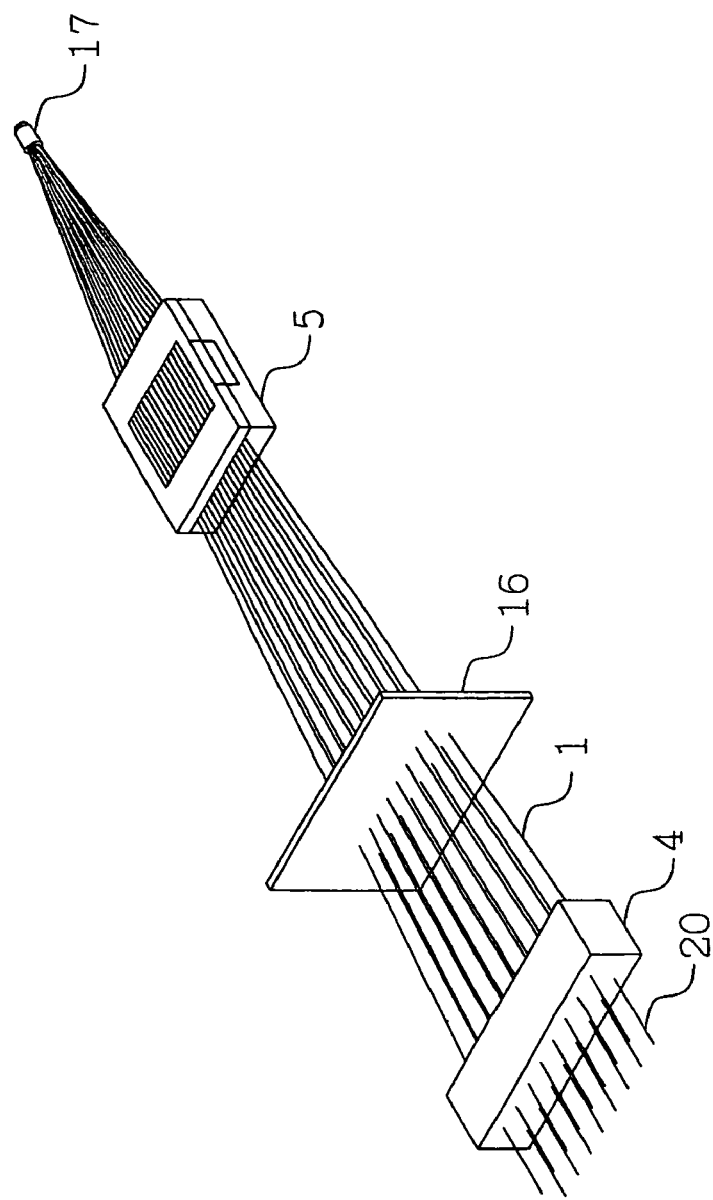
FIG. 1 illustrates the configuration of a capillary array.
Figure 2:
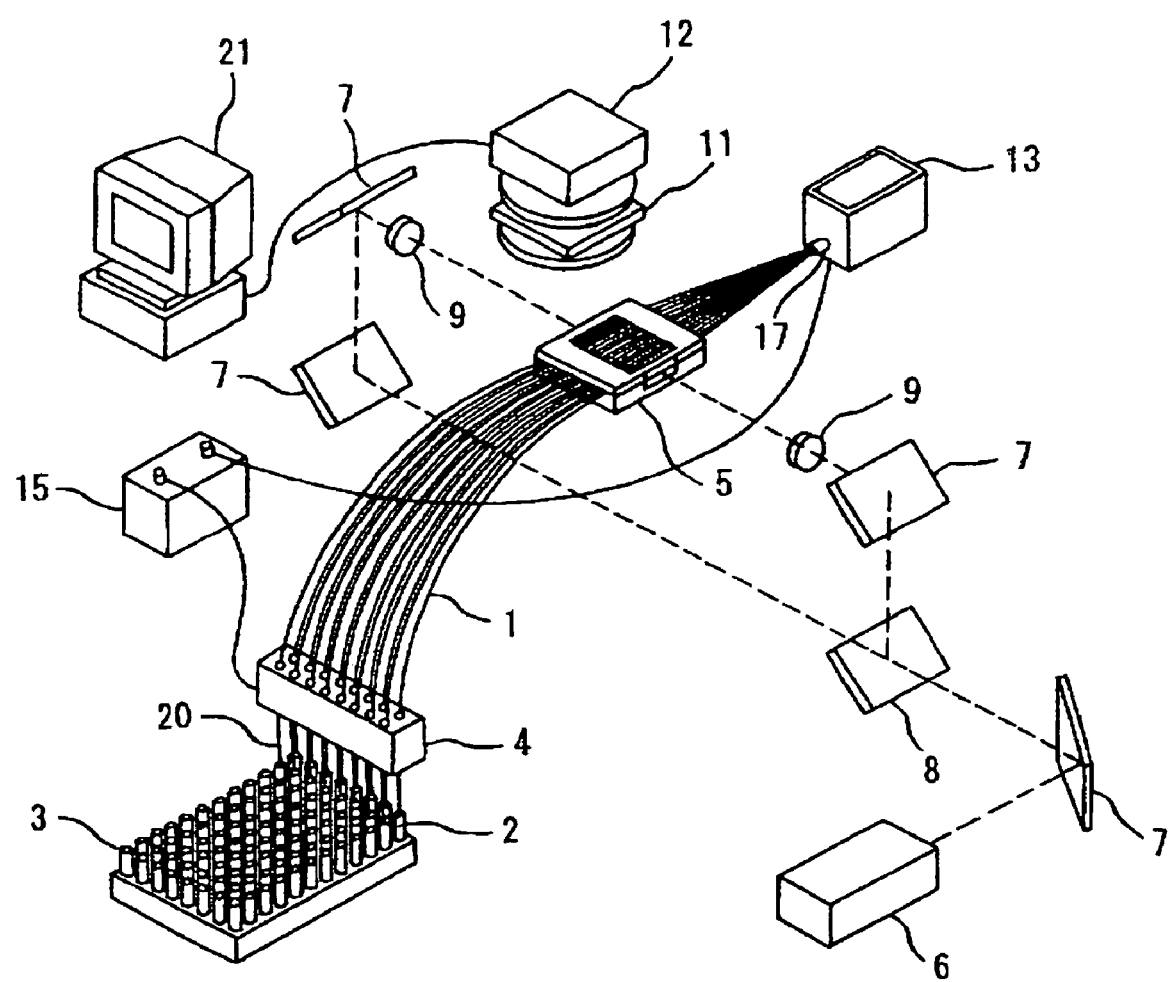
FIG. 2 schematically shows an electrophoresis system.

FIG. 1 shows the configuration of a capillary array. FIG. 2 schematically shows an electrophoresis system. The capillary array and the electrophoresis apparatus including the array will be described by referring to FIGS. 1 and 2.

Normally, a capillary 1 has an external diameter of 0.1 to 0.3 mm and an internal diameter of 0.02 to 0.1 mm, and is coated with a resin such as polyimide resin. The capillary itself is typically made of a quartz pipe, and a capillary array is made by arranging a plurality (typically from several tens to a hundred) of such capillaries.

The electrophoresis system includes an excitation optical system, a detection lens system 11 and a CCD camera 12. A sample tray 3 accommodates many sample containers 2 storing fluorescent-labeled DNA samples measuring 10 to several tens of microliter. A load header 4 loads DNA from the sample tray 3 into the capillaries by electrophoresis. In a detection portion 5, the capillaries are arranged and fixed in place in the order of sample numbers on the load header. The excitation optical system irradiates the capillaries, which are arranged in a plate-like manner, from both sides with an excitation light that is emitted by a laser light source 6 and then focused by a mirror 7, a beam splitter 8, and a focusing lens 9 into approximately the size of the internal diameter of the capillary. Fluorescent light, that is signal light, is detected by the detection lens system. In the illustrated example, the capillary array containing DNA or proteins to be subjected to electrophoresis is irradiated from both sides with laser. The laser is focused by a lens effect of the capillaries such that each and every capillary can be irradiated with the excitation light. Fluorescence emitted by each capillary is detected by the detection optical system. By thus irradiating the array with laser from both sides, each capillary can be excited with uniform intensity. These individual portions together make up a detection unit. The manner of irradiation of the capillary with laser is not limited to the above example and may be instead based on a scan system or a single-batch irradiation system, for example. The scan system employs a galvanometer mirror, for example, for changing the direction of irradiation of laser light. The system might alternatively employ a mirror for reflecting laser light such that by moving the mirror, the capillary that is irradiated with laser light can be switched in a time-division manner. The single-batch system employs a planar divergent beam as excitation light, for example, with which multiple capillaries are simultaneously irradiated. Also, the manner of detection is not limited to the above example and may be instead based on capillary end detection that described in Japanese Patent Application No. 8-188144, for example. In the capillary end detection, the excitation optical system irradiates the excitation light onto the capillaries, and the detection lens system detects the fluorescent light that emitted from the end portion of capillaries.

At the end of the capillary array opposite the load header is located a capillary head 17 in which the multiple capillaries are bundled and glued together, and with which the capillaries are attached to a buffer container 13 containing a buffer, in a pressure- and air-tight manner. To the buffer container and the load header is applied a high voltage of approximately 15 kV from a high-voltage power supply 15, so that the samples in the sample containers can be electrophoresed by the buffer introduced into the capillaries from the buffer container, thereby separating the samples for analysis. The purpose of the load header is to apply a high voltage between the samples and the buffer container using electrodes 20, in addition to the sampling of the samples. The load header and the detection portion 5 may be integrally formed.

The samples as they pass through the gel with which the capillaries are fully filled experience different resistance depending on their size (or length), so that they reach the detecting portion in the order of increasing size. In the detecting portion, the capillaries are irradiated with laser, and fluorescence corresponding to the four nucleoside bases of adenine, guanine, cytosine and thymine emitted by the fluorescence-labeled DNA samples is detected by the CCD camera. The optical signal can be obtained by arranging several tens of the capillaries on an optically flat plane with the accuracy of several microns in height, and then irradiating the plate of capillaries with excitation light from both sides of the plate.

In FIGS. 1 and 2, numeral 16 designates a separator for arranging the multiple capillaries in order, and numeral 21 designates a signal processing and computing unit for performing computations on a detected signal.

Figure 3:
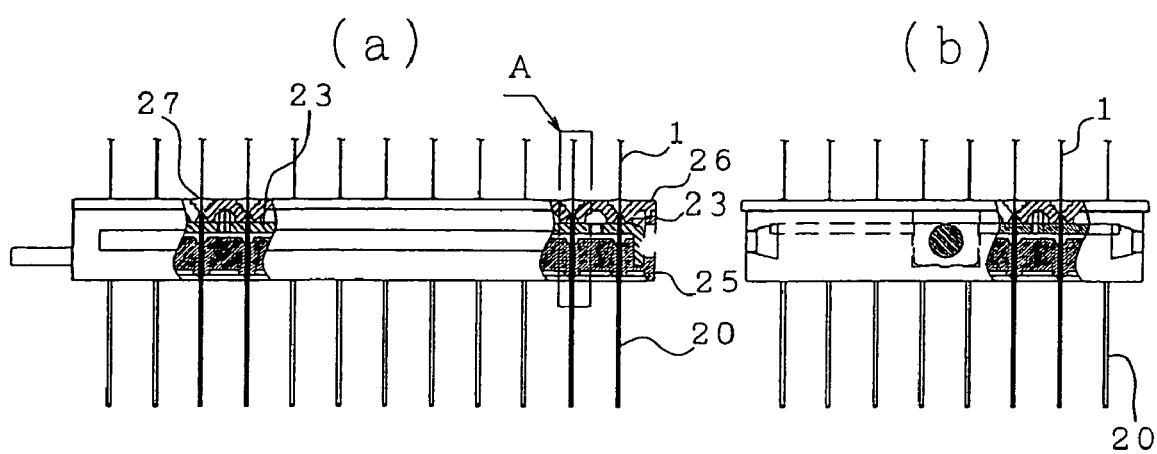
FIG. 3 shows an example of a load header, (a) showing a side view and (b) showing a front view thereof.

FIG. 3 shows an example of the structure of the load header, with (a) showing a side view and (b) showing a front view thereof. Ninety-six capillaries 1 are each inserted into a hollow electrode made of a thin stainless-steel ("SUS") pipe. The tip of the capillaries towards the samples slightly protrudes from the hollow electrode and is fixed in place by an epoxy cement 27 such that the hollow electrode is sealed. The 96 hollow electrodes are electrically connected in advance by means of a connection plate 23, as shown in the figure and at the same time are arranged in order in a holder 25 with strict tolerance. Alternatively, each hollow electrode may be connected to each of the multiple hollow electrodes provided on the apparatus side, without using the connection plate 23. The hollow electrodes made of SUS pipes are used because the samples or reagents used in separation and analysis are corrosive. It goes without saying that the same effects can be obtained by using an electrically conductive plastic in place of the SUS pipes.

The hollow electrodes are fixed in a mold holder made of plastic with a cement and, after assembling the connection plate inside, a lid 26 is joined to the holder by ultrasound, thereby completing the load header.

The capillaries are fixed to the lid with the cement 27 in an air-tight manner in order to prevent the capillaries from slipping out as well as high-voltage leakage. Part of the connection plate is bent by 90° such that it can be connected to a high-voltage probe (not shown) via an opening provided in the holder.

The capillary array is an expendable item that must be discarded after several months of use or after several hundred runs of electrophoresis, when the resolution is lowered.

Figure 4:
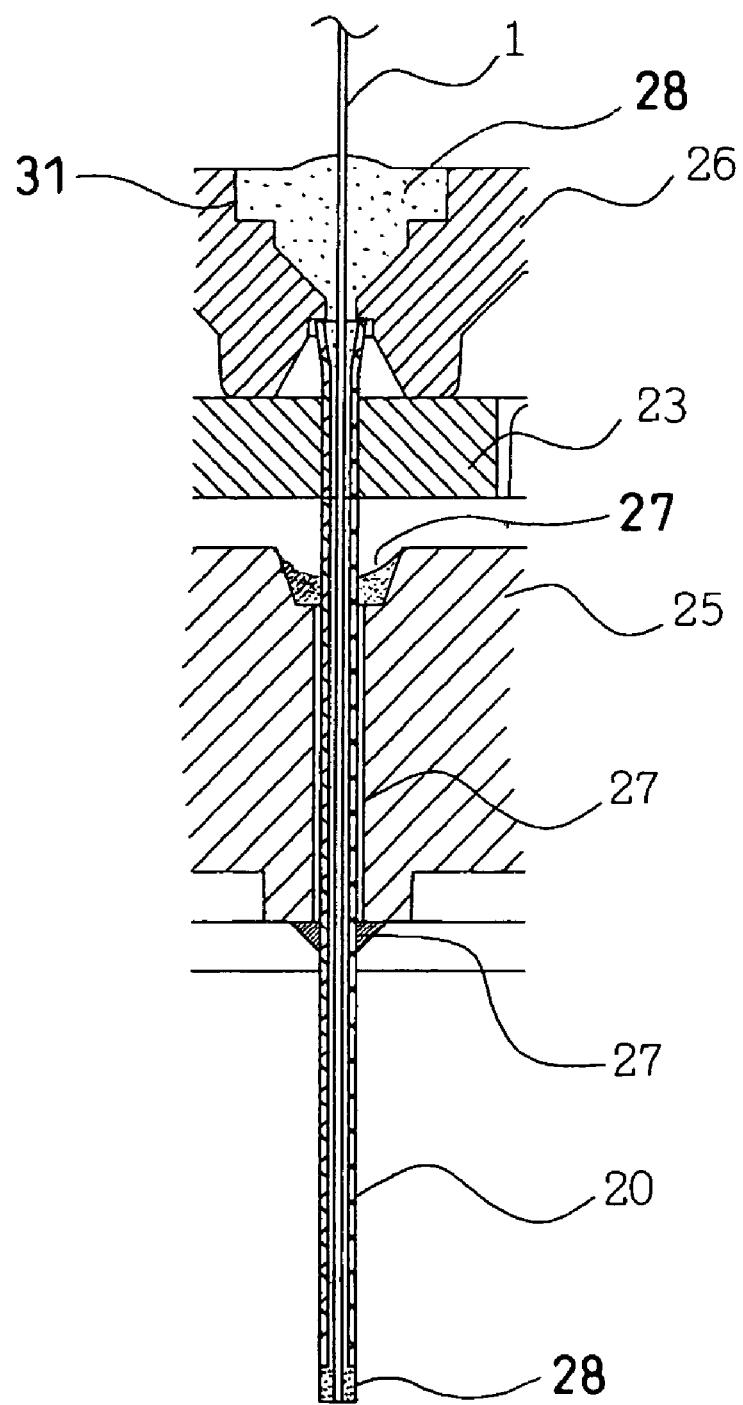
FIG. 4 shows an embodiment of the invention.

FIG. 4 shows a first embodiment of the invention, illustrating an enlarged cross-sectional view of a main portion of the load header. A hollow electrode 20 is fixed to a holder 25 with cement 27. Then, a flare portion of the hollow electrode 20 is passed through an opening in an electrically conductive connection plate 23, thereby electrically connecting the individual electrodes. The lid 26 is then closed and joined with the holder 25 at the periphery by ultrasound, thereby completing the load header. As a funnel-shaped capillary guide opening 31 of the lid 26 is joined concentrically with the hollow electrode 20, the capillary 1 can be easily inserted into the capillary guide opening 31 up to the end of the hollow electrode as it is guided by the flare portion of the hollow electrode 20. The capillary guide opening 31 is then filled with a filling cement 28 such as an epoxy resin, silicon rubber, or silicon rubber gel, as shown in the figure, such that the filling cement can pass through the flare portion of the hollow electrode 20 and reach via the capillary guide opening 31 the lower end of the hollow electrode.

If the gap between the hollow electrode and the capillary is of the order of 0.02 to 0.5 mm, the filling cement hardly permeates the gap. If a low-viscosity cement is used, the cement passes through the gap but drops out of the end of the hollow electrode. Accordingly, a pressure is applied to the filling cement such that it can fill the gap. An improved efficiency can be obtained by providing a negative pressure at the lower end of the hollow electrode. As it is only necessary to suck the filling cement from the lower end of the hollow electrode, the structure of the cement-filling apparatus can be simplified.

Further, by thus filling the gap with the cement using a negative pressure, most of the air bubbles in the filling cement can be removed. After the filling cement has solidified, the volume of the air bubbles remaining in the filling cement decreases, enabling the heat in the capillary to be effectively dissipated.

Thus, the air layer between the capillary and the inside of the hollow electrode can be eliminated, thus enabling the production of a load header that can provide a cooling efficiency that is about 10 times better than that of air. This structure can limit the temperature increases within 10 to 20° C., thus making it possible to conduct stable DNA analysis.

Figure 5:
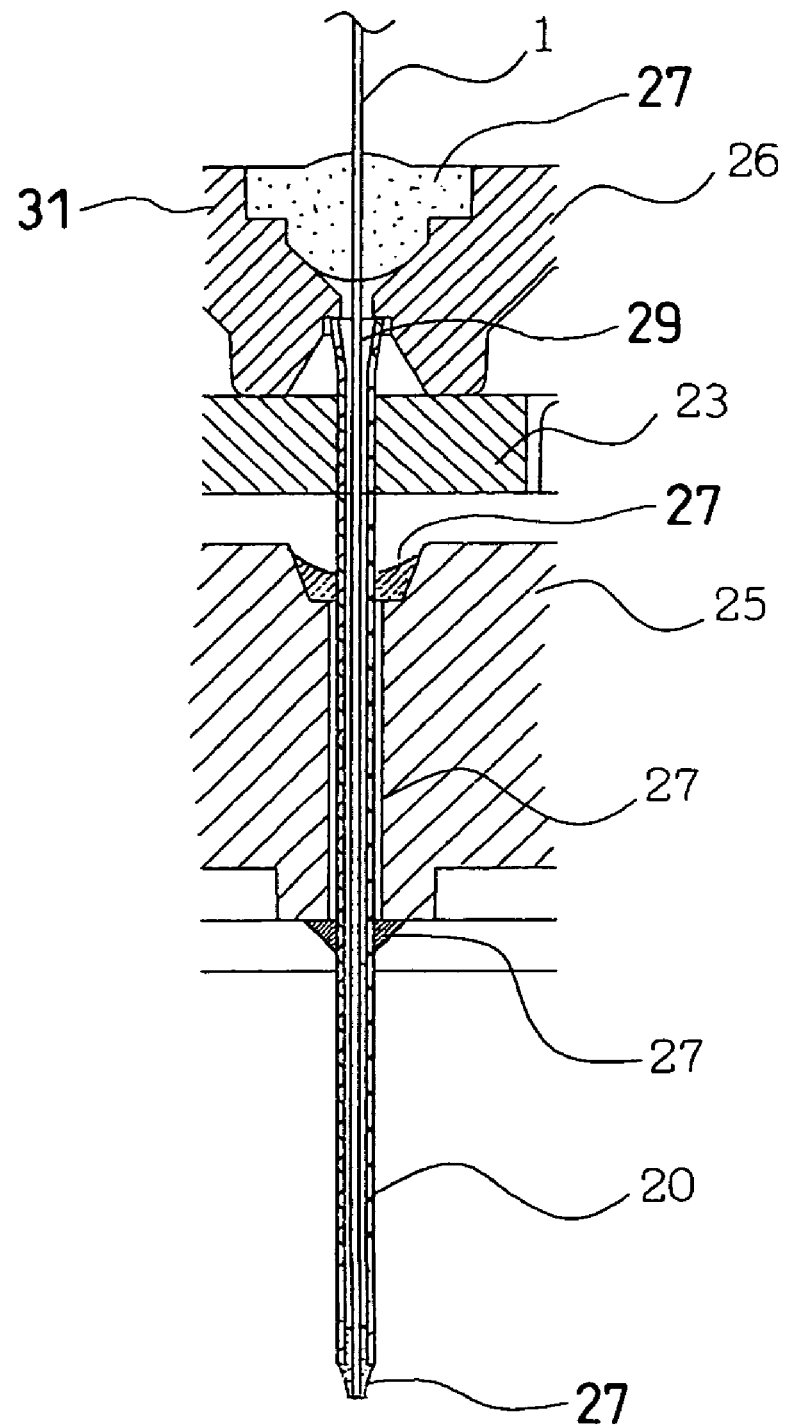
FIG. 5 shows another embodiment of the invention.

FIG. 5 shows another embodiment of the invention, in which the shape of the load header is the same but the manner in which the capillaries are cemented as well as the filling material is different. The capillary 1 is inserted into the capillary guide opening 31 such that the capillary 1 protrudes from the edge of the hollow electrode 20 by approximately 10 mm. The cement 27 is then dispensed at the edge of the hollow electrode such that the hollow electrode 20 and the capillary 1 are cemented together and the hollow electrode edge is sealed. As the cement 27 penetrates into the hollow electrode 20 pipe to the depth of 0.5 to 2.0 mm, sufficient strength can be obtained in the sealed portion. Thereafter, a refrigerating liquid 29, such as water or gel or rubber-like gel containing water, is put into the capillary guide opening 31, which is then sealed with the cement 27.

As will be seen from Table 1, water has a heat conductivity 20 times higher than that of air, so that it can provide a greater cooling efficiency than a resin such as a cement. While the refrigerating liquid hardly exhibits thermal expansion, any expansion of the liquid produced by the temperature rises of 20 to 30° C. can be absorbed by the space enclosed by the lid 26 and the rubber-made conductive connection plate 23. A fluorinated inactive liquid when used as the refrigerating liquid can easily penetrate the gap between the electrode and the capillary due to its excellent permeability. While fluorinated inactive liquids have poorer heat conductivity than water, they have smaller viscosity and can provide similar effects to water in the presence of thermal transfer due to convection.

Figure 6:
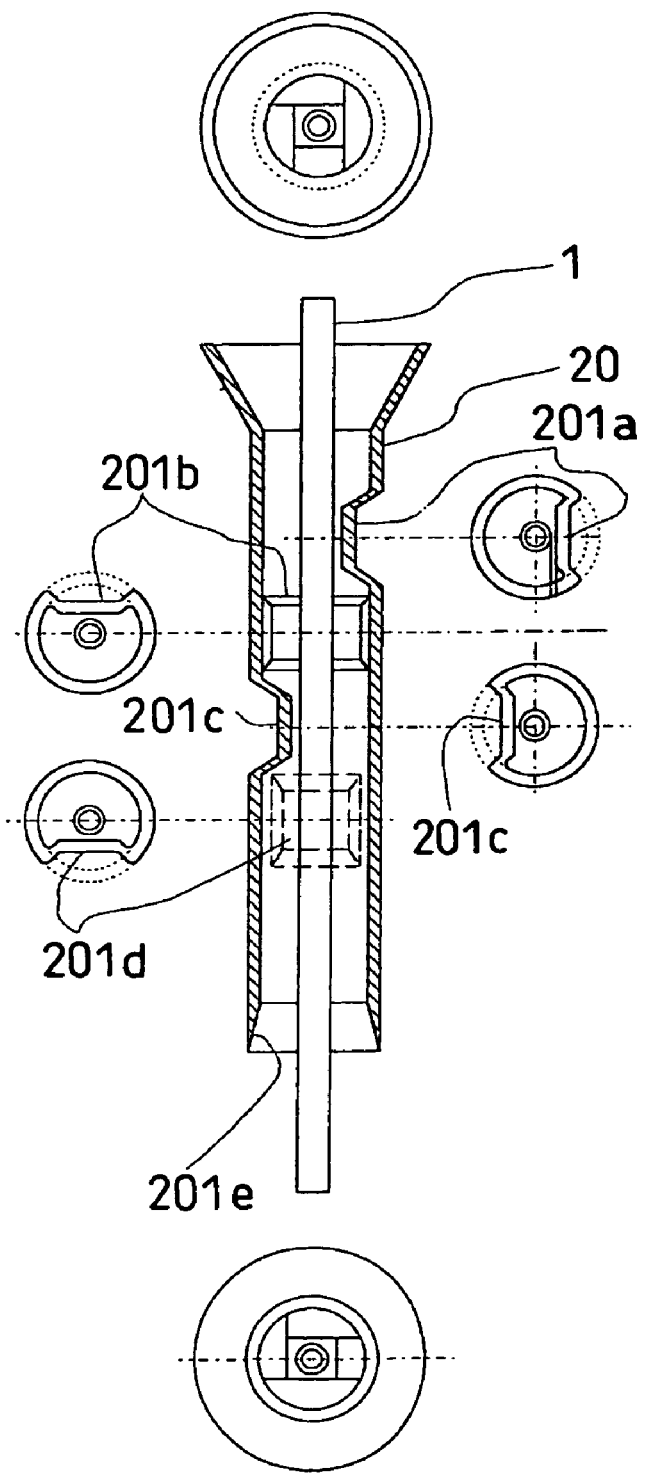
FIG. 6 shows another embodiment of the invention.

Hereafter, an embodiment of the second invention will be described. FIG. 6 shows a hollow electrode axle in which a capillary axle is concentrically disposed such that the heat can be dissipated from the capillary in a uniform manner. Specifically, portions of the hollow electrode pipe are depressed inward at intervals of 90°, thus producing hollow electrode depressed portions 201a to 201d as shown, whereby the capillary can be guided. This embodiment is particularly suitable for hollow electrodes whose internal diameter is 1 mm or less.

Figure 7:
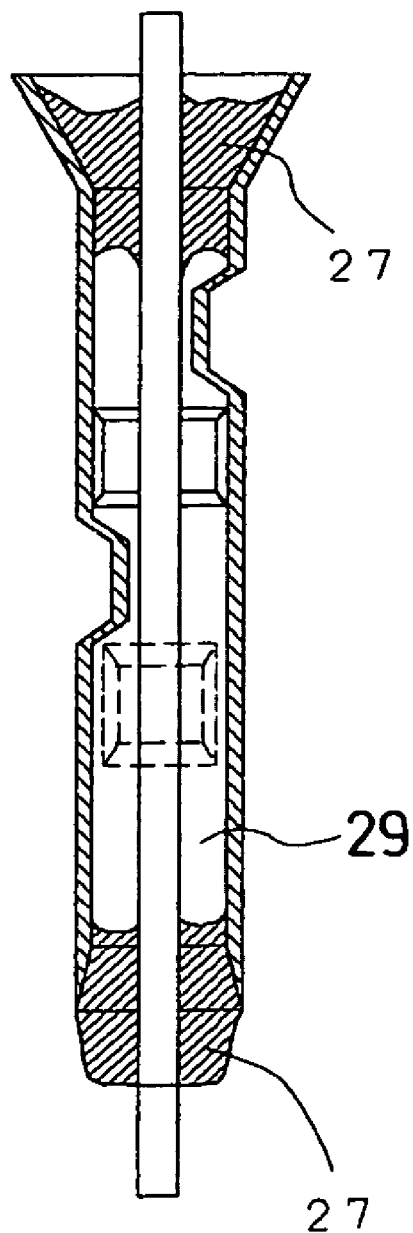
FIG. 7 shows another embodiment of the invention.
Figure 7:
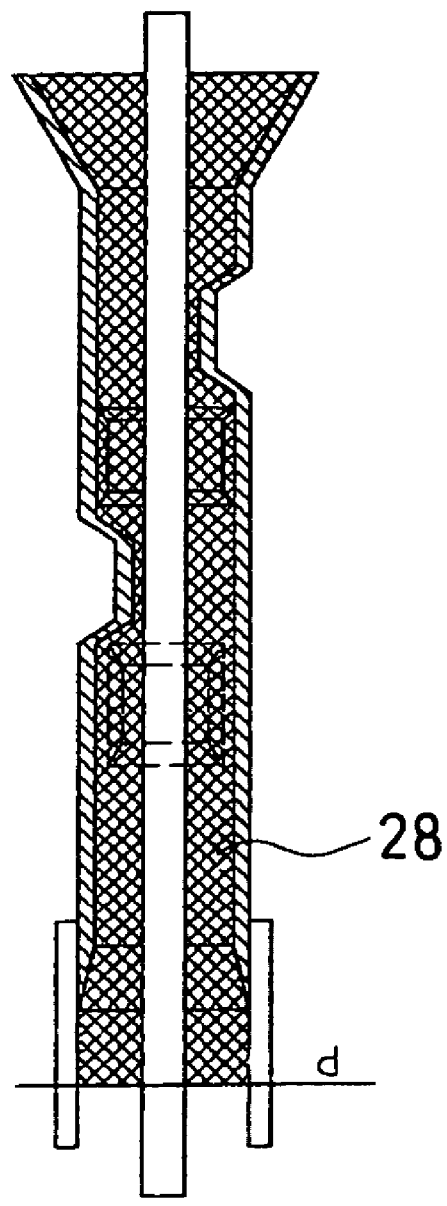

FIG. 7 shows another embodiment of the second invention. FIG. 7a shows the load header of the same structure as shown in FIG. 6, in which the refrigerating liquid 29 is sealed inside with both ends of the hollow electrode sealed with cement. FIG. 7b shows the load header of the structure as shown in FIG. 6, in which the filling cement 28 is filled inside the hollow electrode. In either case, a better heat dissipation can be obtained than the embodiment shown in FIG. 6.

Figure 8:
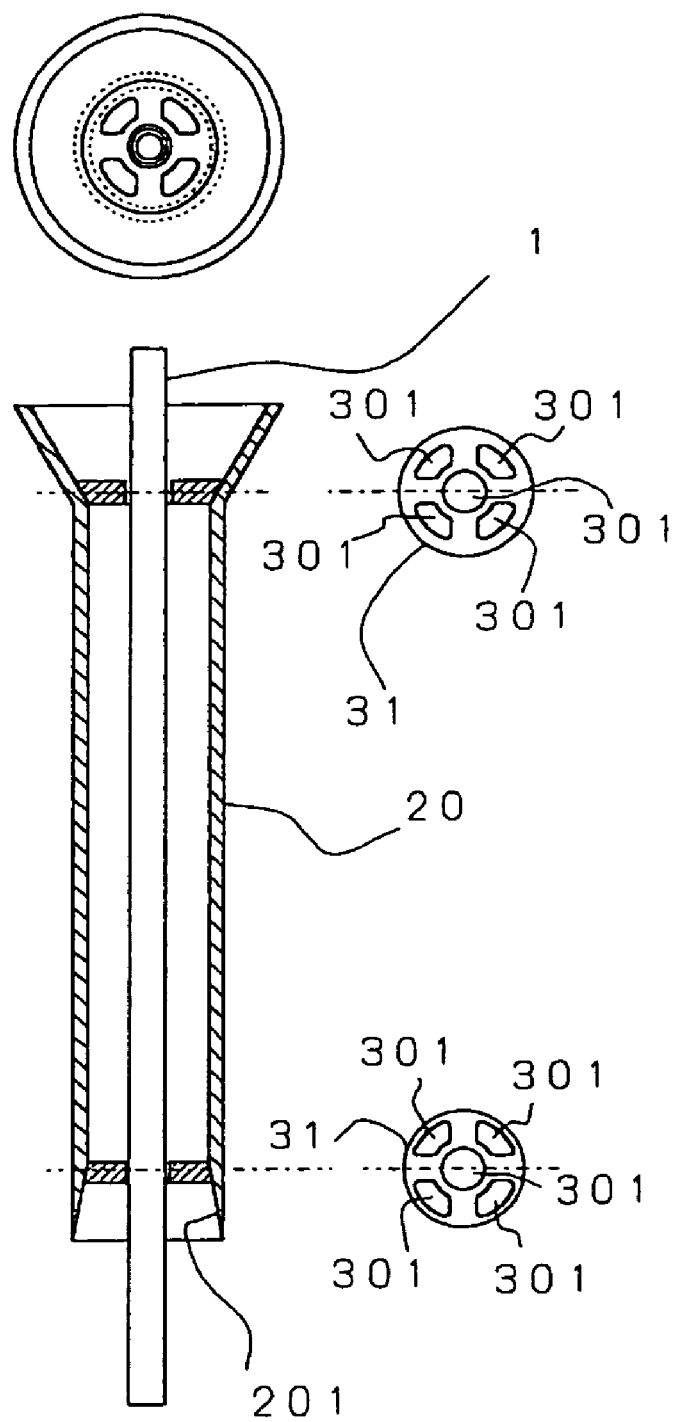
FIG. 8 shows another embodiment of the invention.

FIG. 8 shows another embodiment of the second invention, which is suitable when the internal diameter of the hollow electrode is 1 mm or more. In this embodiment, a ring-shaped guide member 31 that is slightly larger than the internal diameter of the hollow electrode 20 is disposed in the tapered portion at both ends of the hollow electrode. The guide member 31 is provided with a plurality of openings 301 for allowing the passage of the filling cement or refrigerating liquid. The diameter of the center is made larger than the external diameter of the capillary 1 by approximately 10%. In this embodiment, it is particularly effective to make the mounting pitch of the ring-shaped guide member not more than 10 mm or so. At larger pitches, the capillary could loosen and become eccentric, thus reducing the effect.

Figure 9:
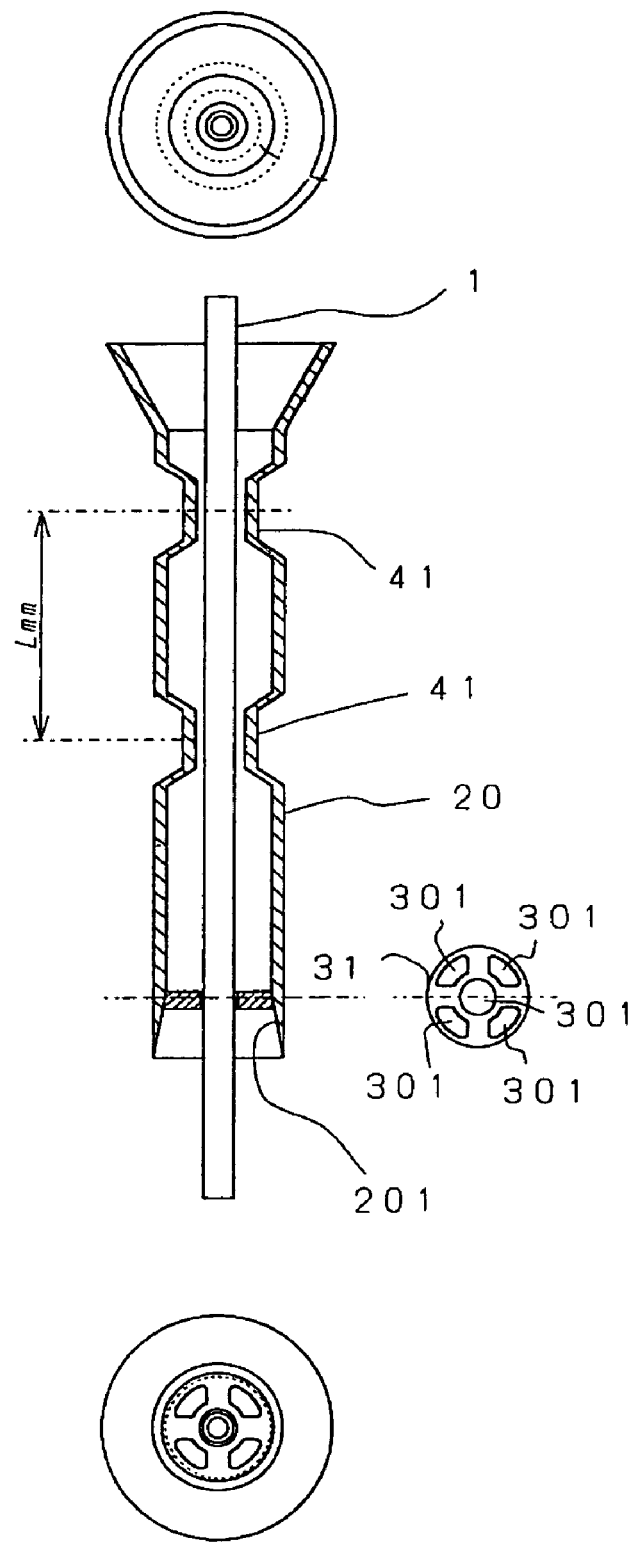
FIG. 9 shows another embodiment of the invention.

FIG. 9 shows yet another embodiment of the second invention. In this example, the hollow electrode pipe is partly squeezed to have reduced pipe diameters. The internal diameter of a narrowed portion 41 is larger than the external diameter of the capillary by 10 to 20%. A ring-shaped guide member 31 is also used at the lower end of the hollow electrode. A filling cement or refrigerating liquid is passed through the hollow electrode.

What is claimed is:
1. A capillary array apparatus comprising:
   a plurality of capillaries;
   a detection portion in which the plurality of capillaries are arranged in parallel;

a load header which retains the capillaries and hollow electrodes at a sample injection end of the capillaries; and a capillary head which retains the plurality of capillaries at the other end of the capillaries, wherein the hollow electrode comprises a plurality of depressed portions which retains the capillary, and wherein the pipe and capillary axis are concentrically disposed, an entire region between each electrode and each capillary is filled with a filling cement and the gap between each of the openings with which the load header is provided and each capillary passing through the opening is filled with the filling cement.

2. The capillary array apparatus according to claim 1, wherein the electrode is made of a metal or electrically conductive plastic pipe.

3. The capillary array apparatus according to claim 1, wherein a guide member is provided on the inside of the hollow electrode for making the capillary axis coincide with the hollow electrode axis.

4. The capillary array apparatus according to claim 1, wherein each capillary passes through the hollow electrode in a non-contact manner, and wherein a heat transfer medium selected from the group consisting of solids, liquids and gels is filled between each hollow electrode and capillary.

* * * * *